United States Patent
Schulte, II et al.

(10) Patent No.: US 10,829,449 B2
(45) Date of Patent: Nov. 10, 2020

(54) METHODS OF MANUFACTURE OF BIS(ETHER ANHYDRIDE)S AND POLYETHERIMIDES

(71) Applicant: SABIC GLOBAL TECHNOLOGIES B.V., Bergen op Zoom (NL)

(72) Inventors: James Patrick Schulte, II, Evansville, IN (US); Tarun Kumar Pal, Bangalore (IN); Meerakani Mohamed Ali Sait, Tamil Nadu (IN)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 3 days.

(21) Appl. No.: 16/087,824

(22) PCT Filed: Mar. 27, 2017

(86) PCT No.: PCT/US2017/024266
§ 371 (c)(1),
(2) Date: Sep. 24, 2018

(87) PCT Pub. No.: WO2017/172593
PCT Pub. Date: Oct. 5, 2017

(65) Prior Publication Data
US 2019/0092726 A1    Mar. 28, 2019

Related U.S. Application Data

(60) Provisional application No. 62/314,546, filed on Mar. 29, 2016.

(51) Int. Cl.
| | | |
|---|---|---|
| *C07D 209/48* | (2006.01) | |
| *C07D 307/89* | (2006.01) | |
| *C09K 21/14* | (2006.01) | |
| *C07C 231/14* | (2006.01) | |
| *C08G 73/10* | (2006.01) | |

(52) U.S. Cl.
CPC .......... *C07D 209/48* (2013.01); *C07C 231/14* (2013.01); *C07D 307/89* (2013.01); *C08G 73/1007* (2013.01); *C08G 73/1053* (2013.01); *C09K 21/14* (2013.01)

(58) Field of Classification Search
CPC .. C07D 209/48; C07D 307/89; C07D 231/02; C07D 231/14; C08G 73/1053; C08G 73/1007
See application file for complete search history.

(56) References Cited

U.S. PATENT DOCUMENTS

| | | |
|---|---|---|
| 3,879,428 A | 4/1975 | Heath et al. |
| 3,957,862 A | 5/1976 | Heath et al. |
| 3,965,125 A | 6/1976 | Meyers |
| 4,020,069 A | 4/1977 | Johnson et al. |
| 4,054,600 A | 10/1977 | Johnson |
| 4,769,476 A * | 9/1988 | Howson ................. C07C 65/24 528/125 |
| 7,813,127 B2 | 10/2010 | Nishikawa et al. |

FOREIGN PATENT DOCUMENTS

CN   101402625 A   4/2009

OTHER PUBLICATIONS

International Search Report for International Application No. PCT/US2017/024266, International Filing Date Mar. 27, 2017, dated Jun. 8, 2017, 5 pages.
Written Opinion for International Application No. PCT/US2017/024266, International Filing Date Mar. 27, 2017, dated Jun. 8, 2017, 6 pages.

* cited by examiner

*Primary Examiner* — Kuo Liang Peng
(74) *Attorney, Agent, or Firm* — Cantor Colburn LLP

(57) ABSTRACT

A method for the manufacture of a bis(ether anhydride) comprises contacting an N-substituted bis(ether phthalimide) with a base under conditions effective to ring open the imides to provide a ring-opened product; and contacting the ring-opened product with an acid under conditions effective to provide a composition comprising the bis(ether anhydride).

18 Claims, No Drawings

METHODS OF MANUFACTURE OF BIS(ETHER ANHYDRIDE)S AND POLYETHERIMIDES

CROSS REFERENCE TO RELATED APPLICATIONS

This application is a National Stage application of PCT/US2017/024266, filed Mar. 27, 2017, which claims the benefit of U.S. Provisional Application No. 62/314,546, filed Mar. 29, 2016, both of which are incorporated by reference in their entirety herein.

BACKGROUND

This disclosure relates to methods of manufacture of bis(ether anhydride) and polyetherimide compositions.

Polyetherimides ("PEIs") are amorphous, transparent, high performance polymers having a glass transition temperature ("Tg") of greater than 180° C. PEIs further have high strength, heat resistance, modulus, and broad chemical resistance, and therefore are widely used in applications as diverse as automotive, telecommunication, aerospace, electrical/electronics, transportation, and healthcare.

A method for the manufacture of PEIs includes phase transfer-catalyzed coupling of a nitro- or chloro-N-substituted phthalimide in the presence of a diol alkali metal salt to produce the corresponding N-substituted bisimide (BI), referred to herein as an N-substituted bis(ether phthalimide) or simply a bis(ether phthalimide). An exchange reaction with phthalic anhydride (PA) produces the corresponding dianhydride (DA), referred to herein as a bis(ether anhydride). Polymerization of the bis(ether anhydride) with a diamino compound provides the polyetherimides.

Alternatively, the N-substituted bis(ether phthalimide)s can be hydrolyzed in an aqueous mixture of an alkali metal hydroxide. The resulting salt of bis(ether phthalic acid) is protonated with acid and then isolated. Subsequent cyclization of bis(ether phthalic acid)s to generate bis(ether anhydride)s is typically accomplished with acetic anhydride. However, the hydrolysis of the N-substituted bis(ether phthalimide)s typically requires either long reaction times (e.g., 18 to 120 hours) or high pressure (e.g., 100 to 170 pounds per square inch (psi)) at elevated temperature (e.g., 160 to 190° C.).

Accordingly, there remains a need in the art for improved synthetic methods that do not employ high pressure or long reaction times to hydrolyze N-substituted bis(ether phthalimide)s to the corresponding bis(ether phthalic acid)s. It would be a further advantage if the methods do not require the isolation of the intermediate bis(ether phthalic acid)s. It would be a still further advantage if the methods do not require the use of acetic anhydride or other reactants to effect the cyclization of bis(ether phthalic acid)s to the bis(ether anhydride)s.

BRIEF DESCRIPTION

A method for the manufacture of a bis(ether anhydride) comprises contacting an N-substituted bis(ether phthalimide) with a base under conditions effective to ring open the imides to provide a ring-opened product; and contacting the ring-opened product with an acid under conditions effective to provide a composition comprising the bis(ether anhydride).

In an embodiment, contacting the ring-opened product with an acid comprises: contacting the ring-opened product with an inorganic acid under conditions effective to hydrolyze amide groups in the ring-opened product to provide a bis(ether phthalic acid); removing the inorganic acid; and heating the bis(ether phthalic acid) to provide a composition comprising the bis(ether anhydride).

DETAILED DESCRIPTION

The inventors hereof have discovered a method for the synthesis of bis(ether anhydride)s by the step-wise hydrolysis and in situ ring closure of N-substituted bis(ether phthalimide)s at atmospheric pressure in a matter of hours, without the use of either acetic anhydride or other agents to convert an ortho-diacid to an anhydride. The method has a number of advantages, including lower equipment cost, shorter times, greater safety, and lower materials costs.

The method is described further below with reference to compounds of formulas (1) to (7). A preferred embodiment shown generally in Scheme 1 with reference to compounds (1a) to (7a).

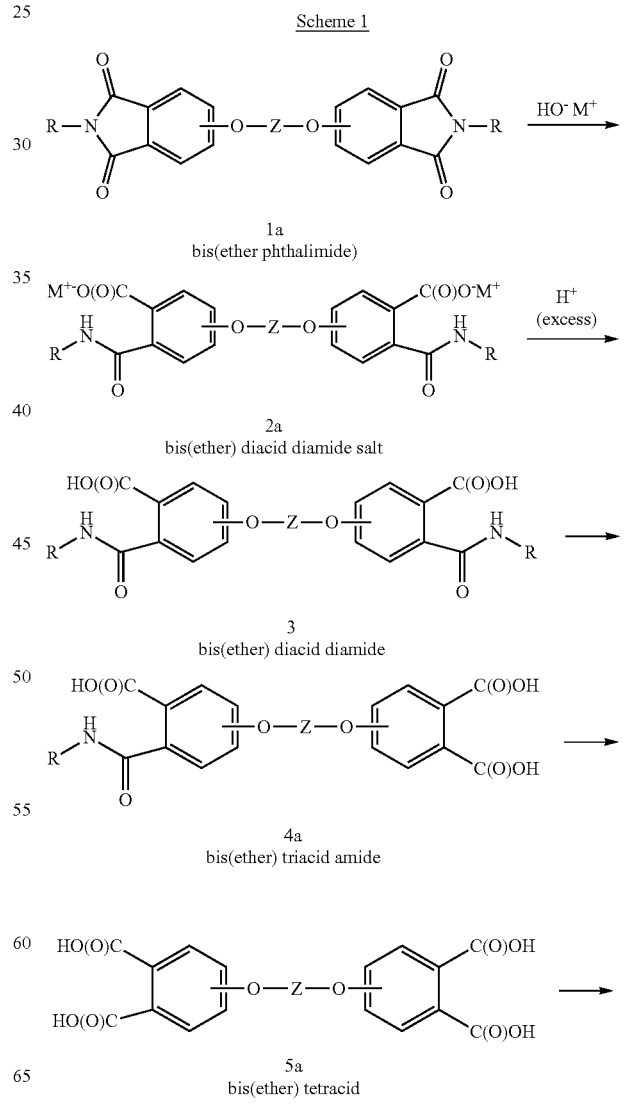

Scheme 1

3
-continued
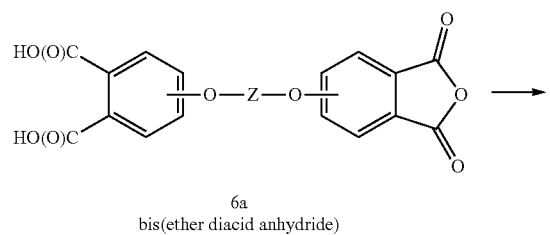
6a
bis(ether diacid anhydride)
4
-continued
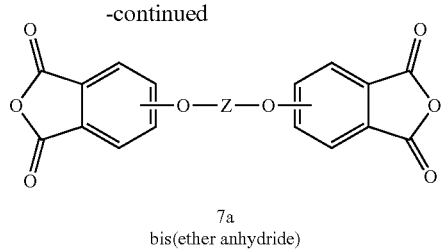
7a
bis(ether anhydride)
A still more preferred embodiment is shown in Scheme 2 with reference to compounds (1b) to (7b).
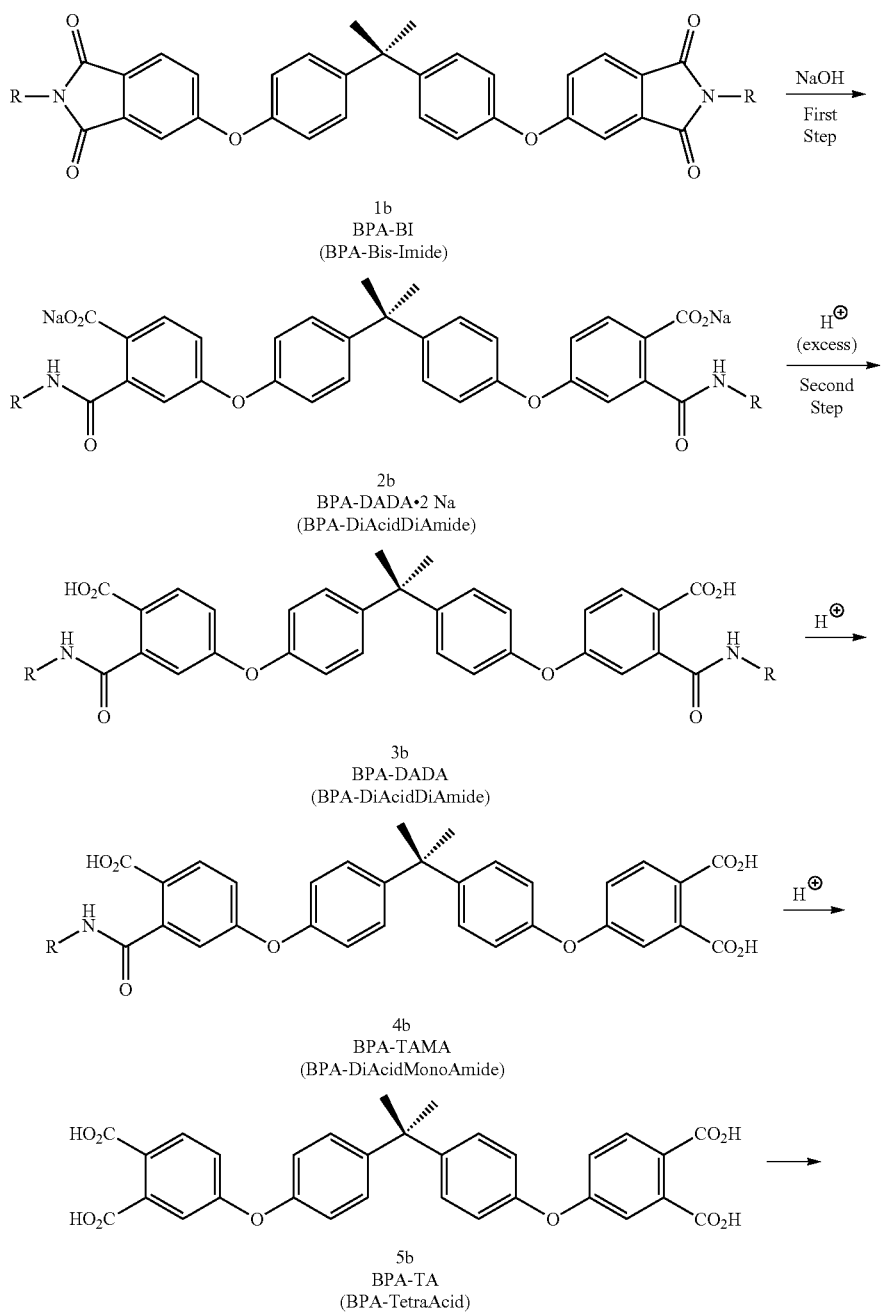

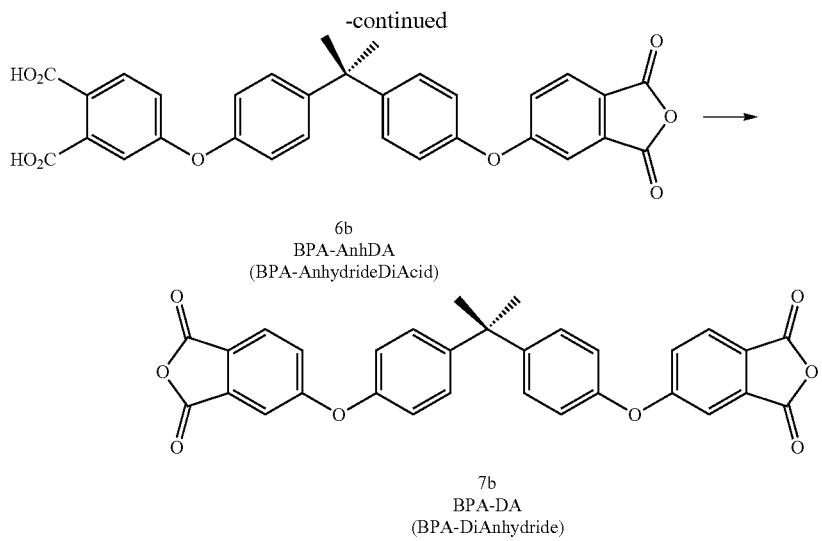

6b
BPA-AnhDA
(BPA-AnhydrideDiAcid)

7b
BPA-DA
(BPA-DiAnhydride)

The starting material is an N-substituted bis(ether phthalimide) (1)

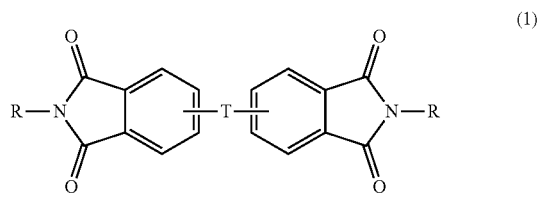

or (1a) in Scheme 1 or (1b) in Scheme 2.

In formulas (1), (1a), and (1b), R is a $C_{1-12}$ alkyl, preferably methyl, an aryl or heteroaryl.

Further in formula (1), T is —O— or a group of the formula —O—Z—O—. In Formulas (1) and (1a), the divalent bonds of the —O— or the —O—Z—O— group are in the 3,3',3,4',4,3', or the 4,4' positions. Exemplary groups Z include groups of formula

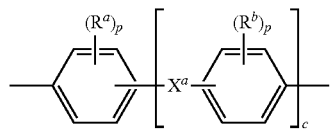

wherein $R^a$ and $R^b$ are each independently the same or different, and are a halogen atom or a monovalent $C_{1-6}$ alkyl group, for example; p and q are each independently integers of 0 to 4; c is 0 to 4; and $X^a$ is a bridging group connecting the hydroxy-substituted aromatic groups, where the bridging group and the hydroxy substituent of each $C_6$ arylene group are disposed ortho, meta, or para (specifically para) to each other on the $C_6$ arylene group. The bridging group $X^a$ can be a single bond, —O—, —S—, —S(O)—, —S(O)$_2$—, —C(O)—, or a $C_{1-18}$ organic bridging group. The $C_{1-18}$ organic bridging group can be cyclic or acyclic, aromatic or non-aromatic, and can further comprise heteroatoms such as halogens, oxygen, nitrogen, sulfur, silicon, or phosphorous. The $C_{1-18}$ organic group can be disposed such that the $C_6$ arylene groups connected thereto are each connected to a common alkylidene carbon or to different carbons of the $C_{1-18}$ organic bridging group. A specific example of a group Z is a divalent group of formula

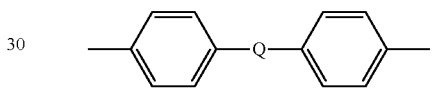

wherein Q is —O—, —S—, —C(O)—, —SO$_2$—, —SO—, or —C$_y$H$_{2y}$— wherein y is an integer from 1 to 5 or a halogenated derivative thereof (including a perfluoroalkylene group). In a specific embodiment Z is a derived from bisphenol A, such that Q is 2,2-isopropylidene.

Methods for the synthesis of bis(ether phthalimide)s (1) and (1a) and (1b) are known.

In the first step of the method, the bis(ether phthalimide) (1) or (1a) or (1b) undergoes ring-opening of the imides. The ring-opened product can be of the salt of the bis(ether) diacid diamide (2)

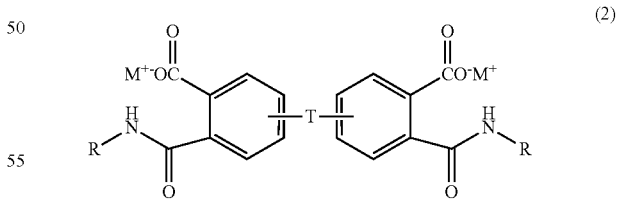

or (2a) in Scheme 1 or (2b) in Scheme 2, wherein R and T are the same as in formulas (1) and (1a), and M in formulas (2) and (2a) is an alkali metal.

In addition to the salt of the bis(ether) diacid diamide (2), the ring-opened product can also include the salt of bis(ether) triacid monoamide (10) and the salt of bis(ether) tetraacid (11)

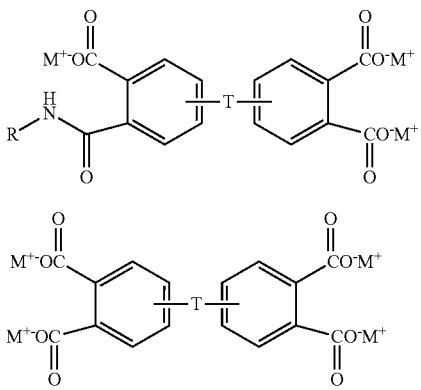

wherein R and T are the same as in formulas (1) and (1a), and M in formulas (10) and (11) is an alkali metal. In an embodiment, the ring-opened product contains greater than 50 wt. %, greater than 60 wt. %, greater than 80 wt. %, or greater than 90 wt. % of the salt of the bis(ether) diacid diamide (2) based on the total weight of the ring-opened product.

The ring opening can be performed in the presence of 1 to 100, 2 to 100, 2 to 50, 2 to 25, 2 to 10, 2 to 5, or to 2 to 4 equivalents of a base, for example an alkali metal hydroxide (such as sodium hydroxide or potassium hydroxide), an alkali carbonate (such as sodium carbonate or potassium carbonate), an alkali bicarbonate (such as sodium bicarbonate or potassium bicarbonate), or a combination comprising at least one of the foregoing, relative to the N-substituted bis(ether phthalimide).

Ring opening is performed under aqueous conditions for an effective amount of time, for example 1 to 10 hours, or 2 to 8 hours, at atmospheric pressure. Organic co-solvents can optionally be added. Exemplary organic solvents include optionally substituted $C_{1-6}$ aliphatic alcohol such as methanol, ethanol, isopropanol, or 1-butanol. Of course, higher pressures can be used, but atmospheric pressure provides cost and convenience advantages. Organic co-solvents can optionally be added.

The ring opening can be conducted at a temperature of 65 to 125 C, or 75 to 120° C., where the temperature refers to reaction media temperature. In an embodiment, the bis(ether phthalimide) (1) or (1a) is heated under reflux to provide the ring-opened product.

The ring opening can be performed with or without a suitable phase transfer catalyst), to generate the salt of the bis(ether) diacid diamide. Exemplary phase transfer catalyst includes a guanadinium salt, a quaternary ammonium salt, a quaternary phosphonium salt, a pyridinium salt, an imidazolium salt, a tertiary amine, a polyether, a glycol ether, or a combination comprising at least one of the foregoing. The amount of the phase transfer catalyst is 0.1 to 8 mole % or 0.2 to 5 mole % based on the total moles of the N-substituted bis(ether phthalimide).

A few of the many phase transfer catalysts that can be used are shown in Table 1.

TABLE 1

| Catalyst | Molecular weight, g/mole |
| --- | --- |
| HEGCl | 263.5 |
| Choline hydroxide | 121.18 |

TABLE 1-continued

| Catalyst | Molecular weight, g/mole |
| --- | --- |
| Choline chloride | 139.62 |
| 1,1,3,3-tetramethylguanidine | 115.18 |
| 1,5-Diazabicyclo-[4,3,0]-non-5-ene | 124.18 |
| Adogen | 464 |
| Tis[2-(2-methoxyethoxy)ethyl]amine | 323.43 |
| 1,8-Diazabicyclo[5,4,0]undec-7-ene | 152.24 |
| Tetrabutylammonium bromide | 322.37 |
| 1,4-Diazabicyclo[2,2,2]octane | 112.17 |
| Tetramethyl glycol dimethyl ether | 222.28 |
| Poly(ethylene glycol) methyl ether | 5000 |
| Polethylene glycol 300 | 300 |
| Triton X-100 | 647 |

The preferred conditions include using bisphenol-A bis-methylimide (1b) at reflux (about 110° C. reaction media temperature) in aqueous NaOH (2-4 equiv of NaOH, such as 3.3 equiv), with hexaethylguanidinium chloride (HEGCl) (1-3 mol % such as 2 mol %), for 2 hours.

The second step of the method includes hydrolysis of the salt of the bis(ether) diacid diamide (2) to ultimately provide the bis(ether anhydride) (7)

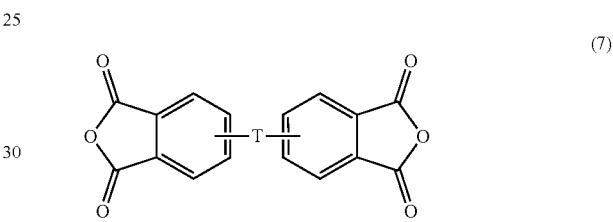

or (7a) in Scheme 1 or (7b) in Scheme 2, wherein T and Z are the same as in formulas (1) and (1a). The alkali metal salt of bis(ether) triacid monoamide (10) and the alkali metal salt of bis(ether) tetraacid (11), if present in the ring-opened product, can also be converted to bis(ether anhydride) (7) under the same process conditions.

Hydrolysis is conducted in the presence of a molar excess of a strong acid (HCl, $H_2SO_4$, $H_3PO_4$, $HNO_3$, or the like). The acid can be present in an amount of 2 to 10 molar equivalents, 3 to 8 molar equivalents, or 4 to 8 molar equivalents based on the total moles of the bis(ether phthalimide) (1) or (1a). In a preferred embodiment, the ring-opened product is not isolated. Thus, hydrolysis can be conducted in the same reaction vessel as ring-opening.

Hydrolysis is carried out in the presence or absence of a non-polar aromatic solvent. Illustrative non-polar aromatic solvent comprises ortho-dichlorobenzene, 1,3-dichlorobenzene, 1,4-dichlorobenzene, benzene, toluene, xylene, dichlorotoluene, 1,2,4-trichlorobenzene, chlorobenzene, bromobenzene, diphenyl sulfone, sulfolane, phenetole, anisole, or a combination comprising at least one of the foregoing. Ortho-dichlorobenzene is specifically mentioned.

Hydrolysis can be conducted at a temperature of 40 to 250° C., 60 to 220° C., or 80 to 200° C., and at atmospheric or higher pressure. For example, an excess of acid, preferably $H_2SO_4$ or HCl with ortho-dichlorobenzene, is added to the salt (2), (2a), or (2b), and the reaction is heated at a temperature of 110 to 190° C. until the desired bis(ether anhydride) (7), (7a), or (7b) is obtained.

Without being bound by theory, it is believed that hydrolysis proceeds via intermediates such as those shown in formula (3a), (4a), (5a), and (6a) in Scheme 1 and those shown in formulas (3b), (4b), (5b), and (6b) in Scheme 2. It is to be understood that hydrolysis likely proceeds via various equilibrium reactions wherein any one or more the intermediates (3a), (4a), (5a), or (6a) or intermediates (6a) or (3b), (4b), (5b), or (6b) are detectable using instruments such as high resolution liquid chromatography. For example, upon addition of acid at moderate temperatures, acid hydrolysis may rapidly generate the bis(ether phthalic acid) (5a) or (5b). It was observed that in 5 to 30 minutes at about 90° C., N-methyl-substituted bis(ether) acid amides reacted with HCl to form a mixture of bis(ether) tetraacid (5a) or (5b) (also referred to as "bis(ether phthalic acid)"), bis(ether) anhydride diacid (6a) or (6b), and bis(ether anhydride) (7), (7a), or (7b) in a ratio of 77:21:1, respectively.

In an embodiment, after the hydrolysis reaction has proceeded the desired time at a temperature of 90 to 140° C. (generally until no further amide groups are detected), most of the excess acids such as HCl and $H_2SO_4$ are removed. For example, the aqueous layer is removed, the organic layer containing the bis(ether phthalic acid) in the reaction vessel is treated repeatedly with deionized water until pH of the aqueous layer is greater than 4, greater than 5 or greater than 6 or until all inorganic acid is removed, and then the mixture is heated at 140 to 220° C. for example at reflux until cyclization is complete (typically 3 hours) to form the bis(ether anhydride). Again, this method does not require the isolation of any intermediates from the mixture in the reaction vessel.

The prepared bis(ether anhydride) can be used to prepare polyetherimides. Polyetherimides can be prepared by any of the methods well known to those skilled in the art, including the reaction of the bis(ether anhydride) of formula (7), with an organic diamine of formula (8)

$$H_2N—R—NH_2 \quad (8)$$

wherein each R is independently the same or different, and is a substituted or unsubstituted divalent organic group, such as a $C_{6-20}$ aromatic hydrocarbon group or a halogenated derivative thereof, a straight or branched chain $C_{2-20}$ alkylene group or a halogenated derivative thereof, a $C_{3-8}$ cycloalkylene group or halogenated derivative thereof, in particular a divalent group of one or more of the following formulae

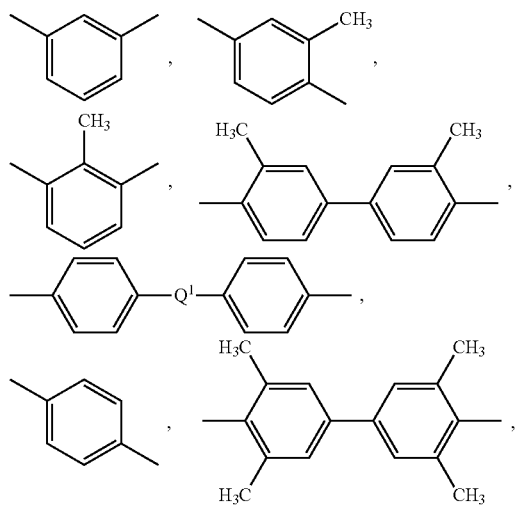

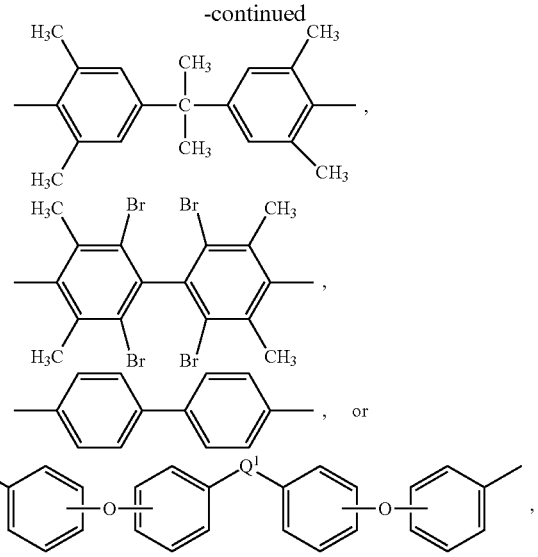

wherein $Q^1$ is —O—, —S—, —C(O)—, —SO_2—, —SO—, —P(R^a)(=O)— wherein $R^a$ is a $C_{1-8}$ alkyl or $C_{6-12}$ aryl, —$C_yH_{2y}$— wherein y is an integer from 1 to 5 or a halogenated derivative thereof (which includes perfluoroalkylene groups), or —$(C_6H_{10})_z$— wherein z is an integer from 1 to 4. In some embodiments R is m-phenylene, p-phenylene, or a diarylene sulfone, in particular bis(4,4'-phenylene)sulfone, bis(3,4'-phenylene)sulfone, bis(3,3'-phenylene)sulfone, or a combination comprising at least one of the foregoing. In some embodiments, at least 10 mole percent or at least 50 mole percent of the R groups contain sulfone groups, and in other embodiments no R groups contain sulfone groups.

Examples of organic diamines include ethylenediamine, propylenediamine, trimethylenediamine, diethylenetriamine, triethylene tetramine, hexamethylenediamine, heptamethylenediamine, octamethylenediamine, nonamethylenediamine, decamethylenediamine, 1,12-dodecanediamine, 1,18-octadecanediamine, 3-methylheptamethylenediamine, 4,4-dimethylheptamethylenediamine, 4-methylnonamethylenediamine, 5-methylnonamethylenediamine, 2,5-dimethylhexamethylenediamine, 2,5-dimethylheptamethylenediamine, 2,2-dimethylpropylenediamine, N-methyl-bis (3-aminopropyl) amine, 3-methoxyhexamethylenediamine, 1,2-bis(3-aminopropoxy) ethane, bis(3-aminopropyl) sulfide, 1,4-cyclohexanediamine, bis-(4-aminocyclohexyl) methane, m-phenylenediamine, p-phenylenediamine, 2,4-diaminotoluene, 2,6-diaminotoluene, m-xylylenediamine, p-xylylenediamine, 2-methyl-4,6-diethyl-1,3-phenylene-diamine, 5-methyl-4,6-diethyl-1,3-phenylene-diamine, benzidine, 3,3'-dimethylbenzidine, 3,3'-dimethoxybenzidine, 1,5-diaminonaphthalene, bis(4-aminophenyl) methane, bis(2-chloro-4-amino-3,5-diethylphenyl) methane, bis(4-aminophenyl) propane, 2,4-bis(p-amino-t-butyl) toluene, bis(p-amino-t-butylphenyl) ether, bis(p-methyl-o-aminophenyl) benzene, bis(p-methyl-o-aminopentyl) benzene, 1,3-diamino-4-isopropylbenzene, bis(4-aminophenyl) sulfide, bis-(4-aminophenyl) sulfone, and bis(4-aminophenyl) ether. Combinations of these compounds can also be used. In some embodiments the organic diamine is m-phenylenediamine, p-phenylenediamine, sulfonyl dianiline, or a combination comprising one or more of the foregoing.

Copolymers of the polyetherimides can be manufactured using a combination of an aromatic bis(ether anhydride) of formula (7) and a different bis(anhydride), for example a bis(anhydride) wherein T does not contain an ether functionality, for example wherein T is a sulfone. Illustrative examples of bis(ether anhydride)s that can be prepared by the foregoing method or used to prepare copolymers the polyetherimides include 3,3-bis[4-(3,4-dicarboxyphenoxy)phenyl]propane dianhydride; 4,4'-bis(3,4-dicarboxyphenoxy)diphenyl ether dianhydride; 4,4'-bis(3,4-dicarboxyphenoxy)diphenyl sulfide dianhydride; 4,4'-bis(3,4-dicarboxyphenoxy)benzophenone dianhydride; 4,4'-bis(3,4-dicarboxyphenoxy)diphenyl sulfone dianhydride; 2,2-bis[4-(2,3-dicarboxyphenoxy)phenyl]propane dianhydride; 4,4'-bis(2,3-dicarboxyphenoxy)diphenyl ether dianhydride; 4,4'-bis(2,3-dicarboxyphenoxy)diphenyl sulfide dianhydride; 4,4'-bis(2,3-dicarboxyphenoxy)benzophenone dianhydride; 4,4'-bis(2,3-dicarboxyphenoxy)diphenyl sulfone dianhydride; 4-(2,3-dicarboxyphenoxy)-4'-(3,4-dicarboxyphenoxy)diphenyl-2,2-propane dianhydride; 4-(2,3-dicarboxyphenoxy)-4'-(3,4-dicarboxyphenoxy)diphenyl ether dianhydride; 4-(2,3-dicarboxyphenoxy)-4'-(3,4-dicarboxyphenoxy)diphenyl sulfide dianhydride; 4-(2,3-dicarboxyphenoxy)-4'-(3,4-dicarboxyphenoxy)benzophenone dianhydride; and, 4-(2,3-dicarboxyphenoxy)-4'-(3,4-dicarboxyphenoxy)diphenyl sulfone dianhydride, as well as various combinations thereof.

The polyetherimides can have a melt index of 0.1 to 10 grams per minute (g/min), as measured by American Society for Testing Materials (ASTM) D1238 at 340 to 370° C., using a 6.7 kilogram (kg) weight. In some embodiments, the polyetherimide polymer has a weight average molecular weight (Mw) of 1,000 to 150,000 grams/mole (Dalton), as measured by gel permeation chromatography, using polystyrene standards. In some embodiments the polyetherimide has an Mw of 10,000 to 80,000 Daltons. Such polyetherimide polymers typically have an intrinsic viscosity greater than 0.2 deciliters per gram (dl/g), or, more specifically, 0.35 to 0.7 dl/g as measured in m-cresol at 25° C.

This disclosure is further illustrated by the following examples, which are non-limiting.

EXAMPLES

The following examples were conducted as illustrated in Scheme 2.

Example 1

A 250 mL, 3-neck round bottom flask was charged with finely ground N-methyl-4,4'-BPA-BI ($C_{33}H_{26}N_2O_6$)/N-methyl-3,4'-BPA-BI ($C_{33}H_{26}N_2O_6$) (96:4 ratio, 10.00 g, 18.30 mmol), water (60 mL), and 4 N aq. NaOH (15 mL, 3.28 equiv). A Dean-Stark trap with condenser and mechanical stirrer were added, and then the reactants were heated to a temperature of 65° C. The reaction temperature was raised to 115° C. and after about 4.5 hours (h), all starting material was consumed. The light yellow homogeneous solution was sampled for ultra-high pressure liquid chromatography (UPLC) analysis, which showed a mixture of the sodium salts of N-methyl-4,4'-BPA-DADA/N-methyl-3,4'-BPA-DADA/N-methyl-4,4'-BPA-TAMA in a 94:3:3 ratio, respectively.

To this mixture at 120° C. was added ortho-dichlorobenzene (o-DCB) ($C_6H_4C_{12}$) (70 mL), followed by 6 N aq. HCl (18.3 mL, 110 mmol, 6 equiv.) whereupon a white precipitate formed. The reaction temperature was increased to 125° C. and stirring continued without nitrogen flow. After about 2 hours the reaction was allowed to cool, the top aqueous layer was removed by pipette, and then back-extracted with o-DCB (50 mL). The organic extract was combined back into the reaction flask. Additional water (60 mL) was added to the reaction flask. The mixture was stirred for 5 min, and then the top aqueous layer was removed again with a pipette. This was continued in like fashion until the aqueous layer tested to a pH of about 6. The reaction mixture was finally washed with a saturated NaCl solution (brine) three times, whereupon a sticky colorless solid precipitated. All aqueous layers were combined, extracted with fresh o-DCB, and the organic layer was returned to the reaction flask.

The reaction mixture was heated to reflux to azeotropically remove water and begin the cyclization. After about 30 minutes, the residual water was collected in the Dean-Starke trap. The reaction mixture became a homogeneous solution and UPLC analysis indicated that the reaction solution was a mixture of 4,4'-BPA-DA (91%), 3,4'-BPA-DA (5%), and 4,4'-BPA-AnhDA (4%). This mixture was next used in the polymerization with m-PD ($C_6H_8N_2$) to make a polyetherimide having a molecular weight of 21.2 kDA, as measured by gel permeation chromatography, using polystyrene standards.

Example 2

A 250 mL, 3-neck round bottom flask was charged with N-methyl-4,4'-BPA-BI($C_{33}H_{26}N_2O_6$)/N-methyl-3,4'-BPA-BI ($C_{33}H_{26}N_2O_6$) (96:4 ratio, 5.00 g, 9.15 mmol), methanol (40 ml), and 4 N aq. NaOH (10.06 mL, 4.4 equiv). A Dean-Stark trap with condenser and mechanical stirrer were added, and then the reactants were heated to a temperature of 85° C. with a light nitrogen sweep. After 15 minutes, all starting material had dissolved to yield a colorless solution. After 45 min, most of the methanol ($CH_4O$) (37.5 mL) had collected in the Dean-Stark trap and water (30 mL) was added to the reaction flask. One hour after heating the mixture, UPLC analysis showed all BPA-BI was consumed and a mixture of the sodium salts of N-methyl-4,4'-BPA-DADA and N-methyl-3,4'-BPA-DADA in a 96:2.2 ratio remained. The reaction temperature was raised to 115° C., after which the reaction was stirred for an additional 45 minutes to drive off the remaining methanol. A mixture of water/methanol (18.0 mL) was drained from the Dean-Stark trap.

To this mixture at 120° C. was added o-DCB ($C_6H_4C_{12}$) (100 mL), followed by 6 N aq. HCl (9.15 mL, 54.9 mmol, 6 equiv.) whereupon a white precipitate formed. The reaction temperature was increased to 135° C. and stirring continued without nitrogen flow. After 20 minutes, most solids had dissolved. After 1.5 hours at 140° C., the reaction temperature was increased to 180° C. to remove water via its azeotrope with the organic solvent. After about 1 hour at 180° C., the water/o-DCB azeotrope (61 mL) was removed from the Dean-Stark flask. Additional o-DCB (50 mL) was added to the reaction, and the reaction temperature was raised to 190° C. After about 1.5 hours at 190° C., o-DCB (46 mL) was drained from the Dean-Stark trap. UPLC analysis indicated that the cyclization was complete and a mixture of 3,4'-BPA-anhdiacid (2%), 3,4'-BPA-DA (4%), and 4,4'-BPA-DA (90%) was present.

Example 3 (Comparative)

A 250 mL, 3-neck round bottom flask was charged with N-methyl-4,4'-BPA-BI($C_{33}H_{26}N_2O_6$)/N-methyl-3,4'-BPA- BI ($C_{33}H_{26}N_2O_6$) (96:4 ratio, 10.00 g, 18.30 mmol), toluene (100 ml), water (24.4 mL), and NaOH (2.93 g, 73.2 mmol, 4 equiv). A condenser and mechanical stirrer were added, and then the reactants were heated to a temperature of 85° C. After two hours at 85° C. starting material remained. Additional 4 N aqueous NaOH (1.8 mL, 7.32 mmol, 0.4 equiv) was added, the mixture heated at 85° C. for 160 min, after which the reaction was not complete. The reaction temperature was then raised to 95° C. and the mixture was stirred for nearly three days. UPLC analysis indicated a mixture of sodium salt of bis(ether phthalic acid), as a minor product (BPA-TA, 17%), with sodium salt of N-methyl-BPA-TAMA (37%), BPA-DADA (39%), and BPA-anhydride diacid (2%).

Example 4

A 100 mL, 3-neck round bottom flask was charged with N-methyl-4,4'-BPA-BI($C_{33}H_{26}N_2O_6$)/N-methyl-3,4'-BPA-BI ($C_{33}H_{26}N_2O_6$) (96:4 ratio, 1.00 g, 1.83 mmol), methanol (20 ml), and 4 N aq. NaOH (2.01 mL, 8.05 mmol, 4.4 equiv). A condenser and mechanical stirrer were added, and then the reactants were heated to a temperature of 75° C. After 30 min. UPLC analysis indicated all starting material was consumed and the disodium salts of N-methyl bis(ether acid amide)s were present in 95% yield.

Example 5

A 250 mL 3-neck round bottom flask was charged with N-methyl-4,4'-BPA-BI($C_{33}H_{26}N_2O_6$)/N-methyl-3,4'-BPA-BI ($C_{33}H_{26}N_2O_6$) (96:4 ratio, 10.00 g, 18.30 mmol), 4 N aq. NaOH (10.06 mL, 2.2 equiv), and water (60 mL). A Dean-Stark trap with condenser and mechanical stirrer were added, the reactants were heated to a temperature of 80° C., and then to 105° C. After 70 min, most material had dissolved and the reaction temperature was raised to 115° C. Two hours later, water (10 mL) was added, and the reaction temperature was raised to 125° C. to help dissolve the remaining solids. After an additional two hours at 125° C., UPLC analysis indicated that mostly the disodium salts of N-methyl bis(ether) acid amides were present. o-DCB (100 mL) and 6 M aq. HCl (9.15 mL) were added to the flask, the reaction temperature was increased to 140° C., and a low nitrogen flow was introduced to azeotropically remove water. Additional o-DCB (50 mL) was added. After 3.5 hours, the Dean-Stark trap was drained of water (59 mL) and o-DCB (64 mL). The reaction solution was then sparged for a few minutes with nitrogen to help remove HCl gas. The mixture of products was then allowed to cool to room temperature and sit overnight.

A sticky white precipitate was observed on the sides of the flask. Water (40 mL) was added and the mixture was stirred for a few minutes. After the layers had settled, a large mass of solid was observed at the bottom of the flask. More 6 M aq. HCl (9.15 mL) was added to the flask and the reactants were heated to a temperature of 90° C. After 15 min, most solids had dissolved. After 90 min total, water (50 mL) was added, the mixture stirred for 20 min, and the layers were allowed to separate. The aqueous layer was removed via pipette. The aqueous layer was extracted with fresh o-DCB (about 30 mL) which was then returned to the reaction flask. The reaction mixture was heated to 135° C. to azeotrope off the remaining water. After nearly 90 min, most solids had dissolved but some remained. Additional water (30 mL) and 6 N aq. HCl (about 9.1 mL) were added and the temperature of the reaction mixture was lowered to 125° C. After 35 min, the stirring was discontinued, the layers were allowed to separate, and the aqueous layer was again removed via pipette.

The temperature of the reaction mixture was raised to 140° C. to remove residual water, after which only trace solid was visible. After 50 min, the temperature of the reaction mixture was raised to 190° C. and a nitrogen sparge was introduced to help concentrate the reaction and remove HCl gas. After 30 min, UPLC analysis indicated that the products present were 4,4'-BPA-DA (95.6%), 4,4'-BPA-AnhDA (4.3%), and 4,4'-BPA-TA (0.1%).

Example 6

A 250 mL round bottom flask with a magnetic stir bar and condenser was charged with N-methyl-4,4'-BPA-BI ($C_{33}H_{26}N_2O_6$)/N-methyl-3,4'-BPA-BI ($C_{33}H_{26}N_2O_6$) (96:4 ratio, 10.00 g, 18.30 mmol), 4 N aq. NaOH (20.13 mL, 4.4 equiv), and 1-butanol ($C_4H_{10}O$) (40 mL). The reactants were heated to 115° C. After 30 min, UPLC analysis indicated all starting material was consumed and mostly N-methyl-BPA-DADA.2Na was present. After 45 min total, the mixture was cooled to room temperature and the layers were allowed to separate. The top organic layer was extracted with water (30 mL) and the combined aqueous layers were placed into a 250 mL 3-neck round bottom flask equipped with a mechanical stirrer, Dean-Stark trap, and condenser. The reaction mixture in this flask was heated at 115° C. to azeotropically remove residual 1-butanol. Additional water (20 mL) was added to the flask.

The distillate was added to the previous organic layer, extracted with fresh water (30 mL), and the aqueous layer was then added back to the reaction flask. After all 1-butanol was distilled off, o-DCB (100 mL) was added, followed by drop-wise addition of 6 N aq. HCl (18.3 mL). Upon settling, the pH of the top (aqueous) layer was 1. Stirring was resumed and the temperature of the reaction mixture was adjusted to 135° C. to begin the azeotropic removal of water. After about 2 hours, the temperature of the reaction mixture was increased to 140° C. Thirty minutes later, additional o-DCB (50 mL) was added to the flask. After another one hour, the temperature of the reaction mixture was increased to 165° C. After 45 minutes later the temperature of the mixture was increased to 195 to 200° C., at which a total of 89 mL of water and 62 mL of o-DCB had been collected in the Dean-Stark trap. After 15 minutes at 195 to 200° C., the reaction was cooled to room temperature and UPLC analysis indicated a mixture of BPA-anhydride diacid (3.5%), 3,4'-BPA-DA (4.6%), and 4,4'-BPA-DA (88.8%).

Example 7

A 3-neck 250 mL round bottom flask with an overhead stirrer, Dean-Starke trap, and condenser was charged with N-Phenyl-3,3'-BPA-BI ($C_{43}H_{30}N_2O_6$)/N-Phenyl-3,4'-BPA-BI ($C_{43}H_{30}N_2O_6$) (96.5:3.5 ratio, 10.00 g, 14.91 mmol), 4 N aq. NaOH (14.91 mL, 4 equiv), and water (60 mL). The reaction mixture was initially heated to t 90° C. and then heated to 105° C. After 17 hours, UPLC analysis indicated all starting material was consumed and a mixture of N-Phenyl-3,3'-BPA-TAMA.3Na (11.7%) and N-Phenyl-BPA-DADA.2Na (84.3%) was present. Water (10 mL) was drained from the trap and o-DCB (70 mL) was added to the reaction flask.

The temperature of the reaction mixture was raised to 115° C., after which 50% aqueous $H_2SO_4$ (17.55 g, 89.46 mmol) was added drop-wise. After the addition was complete, the temperature was raised further to 125° C. and stirring continued for three hours. The heat was removed, stirring was discontinued, and the layers separated within a few minutes. The top aqueous layer was discarded and fresh DI water (100 mL) was added to the flask. The mixture was stirred for one minute, then the layers were allowed to separate and the top aqueous layer was removed. The washing procedure with water was repeated several more times (6×100 mL) until the aqueous layer obtained a pH of 4.

Additional o-DCB (100 mL) was added to the flask and the mixture began heating to 185° C. to remove the water and complete cyclization. After one hour, the temperature reached 180° C. The Dean-Stark trap was drained of the water/o-DCB (30 mL/42 mL) azeotrope, and most solids were dissolved in the light yellow solution. After an additional hour of heating, the flask was allowed to cool to room temperature. The mixture was filtered through a 2.7 μm Whatman GF/D glass microfiber filter paper to obtain a light yellow filtrate. UPLC analysis of the filtrate indicated a mixture of 3,3'-BPA-DA (16.8%), N-Phenyl-3,3'-BPA-anhydrideimide (67.5%), and N-Phenyl-3,3'-BPA-BI (14.9%).

Example 8

The following example is representative of the reactions employing catalysts from Table 1.

A 250 mL 3-neck round bottom flask was charged with finely ground N-methyl-4,4'-BPA-BI ($C_{33}H_{26}N_2O_6$)/N-methyl-3,4'-BPA-BI ($C_{33}H_{26}N_2O_6$) (94:6 ratio, 6.00 g, 11 mmol), water (60 mL), 20% HEGCl in brine (0.3 mL, 0.22 mmol) and solid NaOH (2.2 g, 5 equiv). A condenser and mechanical stirrer were added, and then the reaction mixture was heated to 105° C. The mixture was allowed to stir for 2 h, first a sticky material was formed and then all starting material was consumed. The light yellow homogeneous solution was sampled for UPLC analysis, which showed a mixture of the sodium salts of N-methyl-4,4'-BPA-DADA/N-methyl-3,4'-BPA-DADA/N-methyl-4,4'-BPA-TAMA in a 61:7:21 ratio, respectively.

To a solution of 98% aq. $H_2SO_4$ (3.7 mL, 110 mmol, 6 equiv.) at 90° C. the solution above was added dropwise. After one hour the reaction was allowed to cool, the top aqueous layer was removed by decantation and then the mixture was washed with water twice (2×50 mL) to remove the acid. Additional o-DCB ($C_6H_4Cl_2$) (60 mL) was added to the mixture containing a tacky product, and then a Dean-Stark trap with condenser and mechanical stirrer were affixed to the reaction flask. The reaction mixture was heated to 85° C., and then heated to 180° C. Within 30 minutes all of the tacky material had dissolved. The reaction mixture was heated to reflux to azeotropically remove water during the cyclization. After about 4 h, the residual water was collected in the Dean-Starke trap and UPLC analysis indicated that the reaction solution was a mixture of 4,4'-BPA-DA (87%), 3,4'-BPA-DA (5%), and 4,4'-BPA-AnhDA (8%).

The compositions, methods, and articles can alternatively comprise, consist of, or consist essentially of, any appropriate components or steps herein disclosed. The compositions, methods, and articles can additionally, or alternatively, be formulated so as to be devoid, or substantially free, of any steps, components, materials, ingredients, adjuvants, or species that are otherwise not necessary to the achievement of the function or objectives of the compositions, methods, and articles.

Set forth below are various embodiments of the disclosure.

Embodiment 1

A method for the manufacture of a bis(ether anhydride), the method comprising contacting an N-substituted bis(ether phthalimide) with a base under conditions effective to ring open the imides to provide a ring-opened product; and contacting the ring-opened product with an acid under conditions effective to provide a composition comprising the bis(ether anhydride).

Embodiment 2

The method of Embodiment 1, wherein contacting the N-substituted bis(ether phthalimide) with a base is conducted in the presence of water and optionally an organic co-solvent.

Embodiment 3

The method of Embodiment 2, wherein the organic co-solvent comprises an optionally substituted $C_{1-6}$ aliphatic alcohol.

Embodiment 4

The method of any one or more of the proceeding Embodiments, wherein the base is an alkali hydroxide, an alkali carbonate, an alkali bicarbonate, or a combination comprising at least one of the foregoing.

Embodiment 5

The method of Embodiment 1, wherein the molar ratio of the base relative to the N-substituted bis(ether phthalimide) is 1:1 to 100:1.

Embodiment 6

The method of any one or more of the proceeding Embodiments, wherein contacting the N-substituted bis(ether phthalimide) with a base is conducted in the presence of a phase transfer catalyst.

Embodiment 7

The method of Embodiment 6, wherein the phase transfer catalyst comprises a guanadinium salt, a quaternary ammonium salt, a quaternary phosphonium salt, a pyridinium salt, an imidazolium salt, a tertiary amine, a polyether, a glycol ether, or a combination comprising at least one of the foregoing.

Embodiment 8

The method of Embodiment 6 or Embodiment 7, wherein the phase transfer catalyst is present in an amount of 0.1 to 8 mol %, based on the total moles of the N-substituted bis(ether phthalimide).

Embodiment 9

The method of any one or more of the proceeding Embodiments, wherein contacting an N-substituted bis(ether phthalimide) with a base is conducted at a temperature of 70 to 130° C.

Embodiment 10

The method of any one or more of the proceeding Embodiments, wherein the acid comprises hydrochloric acid, sulfuric acid, nitric acid, phosphoric acid, or a combination comprising at least one of the foregoing.

Embodiment 11

The method of any one or more of the proceeding Embodiments, wherein contacting the ring-opened product with an acid comprises: contacting the ring-opened product with an inorganic acid under conditions effective to hydrolyze amide groups in the ring-opened product to provide a bis(ether phthalic acid); removing the inorganic acid; and heating the bis(ether phthalic acid) to provide a composition comprising the bis(ether anhydride).

Embodiment 12

The method of Embodiment 11, wherein the bis(ether phthalic acid) is formed at a temperature of 90 to 140° C.

Embodiment 13

The method of Embodiment 11 or Embodiment 12, wherein heating the bis(ether phthalic acid) is carried out at a temperature of 140 to 220° C.

Embodiment 14

The method of any one of more of Embodiments 11 to 13, wherein contacting the ring-opened product with the inorganic acid is conducted in the presence of a non-polar aromatic solvent comprising ortho-dichlorobenzene, 1,3-dichlorobenzene, 1,4-dichlorobenzene, benzene, toluene, xylene, dichlorotoluene, 1,2,4-trichlorobenzene, chlorobenzene, bromobenzene, diphenyl sulfone, sulfolane, phenetole, anisole, or a combination comprising at least one of the foregoing.

Embodiment 15

The method of any one or more of the proceeding Embodiments, further comprising heating the composition comprising the bis(ether anhydride) to convert additional bis(ether phthalic acid) to the bis(ether anhydride).

Embodiment 16

The method of any one or more of the preceding Embodiments, wherein the N-substituted bis(ether phthalimide) is of the formula

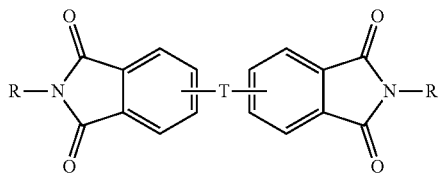

and the bis(ether anhydride) is of the formula

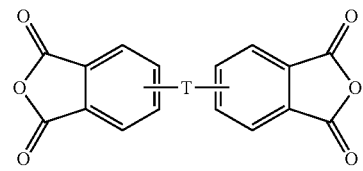

wherein in the foregoing formulas, R is a $C_{1-5}$ alkyl, preferably methyl; and T is —O— or a group of the formula —O—Z—O—, wherein Z is of the formula

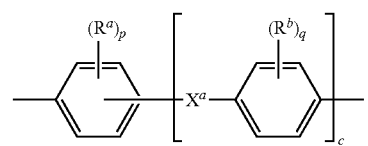

wherein $R^a$ and $R^b$ are each independently a halogen atom or a monovalent $C_{1-6}$ alkyl group; p and q are each independently integers of 0 to 4; c is 0 to 4; and $X^a$ is a bridging group connecting the hydroxy-substituted aromatic groups, where the bridging group and the hydroxy substituent of each $C_6$ arylene group are disposed ortho, meta, or para to each other on the $C_6$ arylene group, preferably wherein the bridging group $X^a$ is a single bond, —O—, —S—, —S(O)—, —S(O)$_2$—, —C(O)—, or a $C_{1-18}$ organic bridging group, and preferably wherein Z is a divalent group of formula

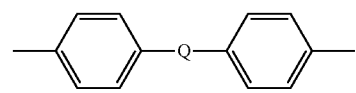

wherein Q is —O—, —S—, —C(O)—, —SO$_2$—, —SO—, or —C$_y$H$_{2y}$— wherein y is an integer from 1 to 5 or a halogenated derivative thereof.

Embodiment 17

The method of any one or more of the preceding Embodiments, wherein the ring-opened product comprises a bis(ether) diacid diamide salt of the formula

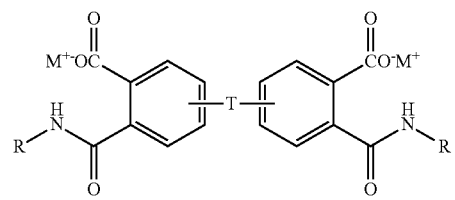

and optionally a bis(ether) triacid amide salt of the formula

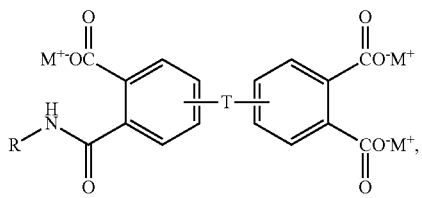

and optionally a bis(ether) tetracid salt of the formula

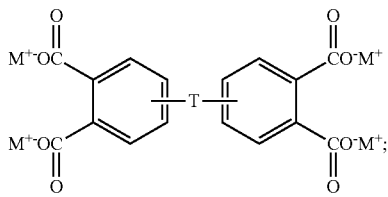

wherein in the in the foregoing formulas, R is a $C_{1-12}$ alkyl, preferably methyl, aryl or heteroaryl; M is an alkaline metal; and T is —O— or a group of the formula —O—Z—O—, wherein Z is of the formula

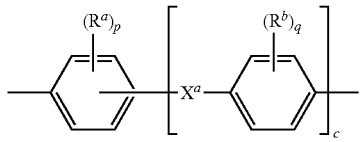

wherein $R^a$ and $R^b$ are each independently a halogen atom or a monovalent $C_{1-6}$ alkyl group; p and q are each independently integers of 0 to 4; c is 0 to 4; and $X^a$ is a bridging group connecting the hydroxy-substituted aromatic groups, where the bridging group and the hydroxy substituent of each $C_6$ arylene group are disposed ortho, meta, or para to each other on the $C_6$ arylene group, preferably wherein the bridging group $X^a$ is a single bond, —O—, —S—, —S(O)—, —S(O)$_2$—, —C(O)—, or a $C_{1-18}$ organic bridging group, and preferably wherein Z is a divalent group of formula

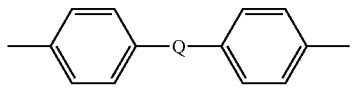

wherein Q is —O—, —S—, —C(O)—, —SO$_2$—, —SO—, or —C$_y$H$_{2y}$— wherein y is an integer from 1 to 5 or a halogenated derivative thereof.

Embodiment 18

The method of Embodiment 16 or 17, wherein Z is 2,2-(4-phenylene)isopropylidene.

Embodiment 19

A method for the manufacture of a polyetherimide composition, the method comprising manufacturing a bis(ether anhydride) in accordance with a method of any or more of the proceeding Embodiments; polymerizing the bis(ether anhydride) and a diamine to provide a polyetherimide composition.

Embodiment 20

A polyetherimide composition manufactured by the method of Embodiment 19.

All ranges disclosed herein are inclusive of the endpoints, and the endpoints are independently combinable with each other (e.g., ranges of "up to 25 wt. %, or, more specifically, 5 wt. % to 20 wt. %", is inclusive of the endpoints and all intermediate values of the ranges of "5 wt. % to 25 wt. %," etc.). "Combinations" is inclusive of blends, mixtures, alloys, reaction products, and the like. The terms "first," "second," and the like, do not denote any order, quantity, or importance, but rather are used to denote one element from another. The terms "a" and "an" and "the" do not denote a limitation of quantity, and are to be construed to cover both the singular and the plural, unless otherwise indicated herein or clearly contradicted by context. "Or" means "and/or" unless clearly stated otherwise. Reference throughout the specification to "some embodiments," "an embodiment," and so forth, means that a particular element described in connection with the embodiment is included in at least one embodiment described herein, and may or may not be present in other embodiments. In addition, it is to be understood that the described elements may be combined in any suitable manner in the various embodiments.

Unless defined otherwise, technical and scientific terms used herein have the same meaning as is commonly understood by one of skill in the art to which this application belongs. All cited patents, patent applications, and other references are incorporated herein by reference in their entirety. However, if a term in the present application contradicts or conflicts with a term in the incorporated reference, the term from the present application takes precedence over the conflicting term from the incorporated reference.

The term "alkyl" means a branched or straight chain, unsaturated aliphatic hydrocarbon group, e.g., methyl, ethyl, n-propyl, i-propyl, n-butyl, s-butyl, t-butyl, n-pentyl, s-pentyl, and n- and s-hexyl. "Alkenyl" means a straight or branched chain, monovalent hydrocarbon group having at least one carbon-carbon double bond (e.g., ethenyl (—HC=CH$_2$)). "Alkoxy" means an alkyl group that is linked via an oxygen (i.e., alkyl-O—), for example methoxy, ethoxy, and sec-butyloxy groups. "Alkylene" means a straight or branched chain, saturated, divalent aliphatic hydrocarbon group (e.g., methylene (—CH$_2$—) or, propylene (—(CH$_2$)$_3$—)). "Cycloalkylene" means a divalent cyclic alkylene group, —C$_n$H$_{2n-x}$, wherein x is the number of hydrogens replaced by cyclization(s). "Cycloalkenyl" means a monovalent group having one or more rings and one or more carbon-carbon double bonds in the ring, wherein all ring members are carbon (e.g., cyclopentyl and cyclohexyl). "Aryl" means an aromatic hydrocarbon group containing the specified number of carbon atoms, such as phenyl, tropone, indanyl, or naphthyl. The prefix "halo" means a group or compound including one more of a fluoro, chloro, bromo, or iodo substituent. A combination of different halo groups (e.g., bromo and fluoro), or only chloro groups can be present. The prefix "hetero" means that the compound or group includes at least one ring member that is a heteroatom (e.g., 1, 2, or 3 heteroatom(s)), wherein the heteroatom(s) is each independently N, O, S, Si, or P. "Substituted" means that the compound or group is substituted with at least one (e.g., 1, 2, 3, or 4) substituents that can each independently be a $C_{1-9}$ alkoxy, a $C_{1-9}$ haloalkoxy, a nitro (—$NO_2$), a cyano (—CN), a $C_{1-6}$ alkyl sulfonyl (—S(=O)$_2$-alkyl), a $C_{6-12}$ aryl sulfonyl (—S(=O)$_2$-aryl) a thiol (—SH), a thiocyano (—SCN), a tosyl ($CH_3C_6H_4SO_2$—), a $C_{3-12}$ cycloalkyl, a $C_{2-12}$ alkenyl, a $C_{5-12}$ cycloalkenyl, a $C_{6-12}$ aryl, a $C_{7-13}$ arylalkylene, a $C_{4-12}$ heterocycloalkyl, and a $C_{3-12}$ heteroaryl instead of hydrogen, provided that the substituted atom's normal valence is not exceeded. The number of carbon atoms indicated in a group is exclusive of any substituents. For example —$CH_2CH_2CN$ is a $C_2$ alkyl group substituted with a nitrile.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

The invention claimed is:

1. A method for the manufacture of a bis(ether anhydride), the method comprising
contacting an N-substituted bis(ether phthalimide) with a base under conditions effective to ring open the N-substituted bis(ether phthalimide) to provide a ring-opened product wherein the ring-opened product comprises a bis(ether) diacid diamide salt of the formula

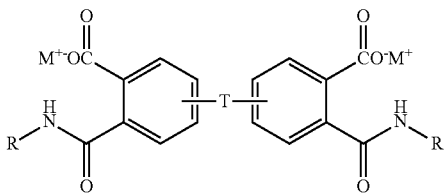

and
optionally a bis(ether) triacid amide salt of the formula

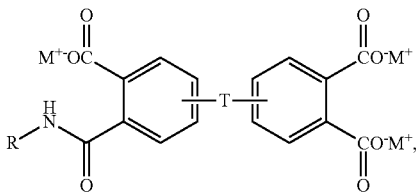

and
optionally a bis(ether) tetracid salt of the formula

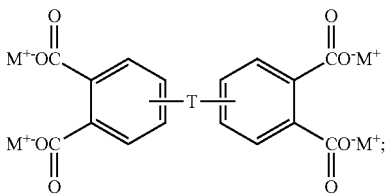

wherein in the foregoing formulas,
R is a $C_{1-12}$ alkyl;
M is an alkaline metal; and
T is —O— or a group of the formula —O—Z—O—, wherein
Z is of the formula

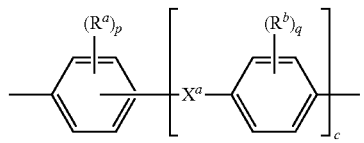

wherein
$R^a$ and $R^b$ are each independently a halogen atom or a monovalent $C_{1-6}$ alkyl group;
p and q are each independently integers of 0 to 4;
c is 0 to 4; and $X^a$ is a bridging group connecting the ether-substituted aromatic groups, where the bridging group and the ether substituent of each $C_6$ arylene group are disposed ortho, meta, or para to each other on the $C_6$ arylene group; and
contacting the ring-opened product with an acid under conditions effective to provide a composition comprising the bis(ether anhydride).

2. The method of claim 1, wherein contacting the N-substituted bis(ether phthalimide) with a base is conducted in the presence of water and optionally an organic co-solvent.

3. The method of claim 2, wherein the organic co-solvent comprises an optionally substituted $C_{1-6}$ aliphatic alcohol.

4. The method of claim 1, wherein the base is an alkali hydroxide, an alkali carbonate, an alkali bicarbonate, or a combination comprising at least one of the foregoing.

5. The method of claim 1, wherein the molar ratio of the base relative to the N-substituted bis(ether phthalimide) is 1:1 to 100:1.

6. The method of claim 1, wherein contacting the N-substituted bis(ether phthalimide) with a base is conducted in the presence of a phase transfer catalyst.

7. The method of claim 6, wherein the phase transfer catalyst comprises a guanadinium salt, a quaternary ammonium salt, a quaternary phosphonium salt, a pyridinium salt, an imidazolium salt, a tertiary amine, a polyether, a glycol ether, or a combination comprising at least one of the foregoing.

8. The method of claim 6, wherein the phase transfer catalyst is present in an amount of 0.1 to 8 mol %, based on the total moles of the N-substituted bis(ether phthalimide).

9. The method of claim 1, wherein contacting an N-substituted bis(ether phthalimide) with a base is conducted at a temperature of 70 to 130° C.

10. The method of claim 1, wherein the acid comprises hydrochloric acid, sulfuric acid, nitric acid, phosphoric acid, or a combination comprising at least one of the foregoing.

11. The method of claim 1, wherein contacting the ring-opened product with an acid comprises:
contacting the ring-opened product with an inorganic acid under conditions effective to hydrolyze amide groups in the ring-opened product to provide a bis(ether phthalic acid);
removing the inorganic acid; and
heating the bis(ether phthalic acid) to provide a composition comprising the bis(ether anhydride).

12. The method of claim 11, wherein the bis(ether phthalic acid) is formed at a temperature of 90 to 140° C.

13. The method of claim 11, wherein heating the bis(ether phthalic acid) is carried out at a temperature of 140 to 220° C.

14. The method of claim 1, wherein contacting the ring-opened product with the inorganic acid is conducted in the presence of a non-polar aromatic solvent comprising ortho-dichlorobenzene, 1,3-dichlorobenzene, 1,4-dichlorobenzene, benzene, toluene, xylene, dichlorotoluene, 1,2,4-trichlorobenzene, chlorobenzene, bromobenzene, diphenyl sulfone, sulfolane, phenetole, anisole, or a combination comprising at least one of the foregoing.

15. The method of claim 1, further comprising heating the composition comprising the bis(ether anhydride) to convert additional bis(ether phthalic acid) to the bis(ether anhydride).

16. The method of claim 1, wherein the N-substituted bis(ether phthalimide) is of the formula

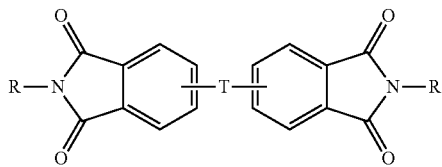

and the bis(ether anhydride) is of the formula

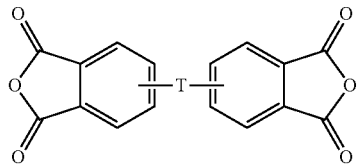

wherein in the foregoing formulas,

R is a $C_{1-5}$ alkyl; and

T is —O— or a group of the formula —O—Z—O—, wherein

Z is of the formula

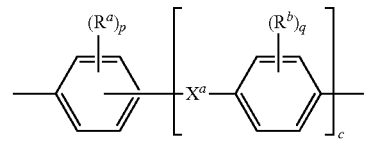

wherein $R^a$ and $R^b$ are each independently a halogen atom or a monovalent $C_{1-6}$ alkyl group;

p and q are each independently integers of 0 to 4;

c is 0 to 4; and $X^a$ is a bridging group connecting the ether-substituted aromatic groups, where the bridging group and the ether substituent of each $C_6$ arylene group are disposed ortho, meta, or para to each other on the $C_6$ arylene group.

17. The method of claim 16, wherein Z is 2,2-(4-phenylene)isopropylidene.

18. A method for the manufacture of a polyetherimide composition, the method comprising manufacturing a bis(ether anhydride) in accordance with a method of claim 1; and polymerizing the bis(ether anhydride) and a diamine to provide a polyetherimide composition.

* * * * *